(12) United States Patent
Liang et al.

(10) Patent No.: US 8,362,070 B2
(45) Date of Patent: Jan. 29, 2013

(54) APPLICATION OF PUERARIN IN THE PREPARATION OF P2X$_3$ MEDIATED DRUGS FOR PAIN/NERVOUS SYSTEM DISEASES

(75) Inventors: Shangdong Liang, Jiangxi (CN); Changshui Xu, Jiangxi (CN); Yun Gao, Jiangxi (CN); Guilin Li, Jiangxi (CN); Jiari Lin, Jiangxi (CN); Shuangmei Liu, Jiangxi (CN); Han Liu, Jiangxi (CN); Jun Zhang, Jiangxi (CN); Xin Li, Jiangxi (CN)

(73) Assignee: Nanchang University, Nanchang, Jiangxi (CN)

( * ) Notice: Subject to any disclaimer, the term of this patent is extended or adjusted under 35 U.S.C. 154(b) by 138 days.

(21) Appl. No.: 12/922,245

(22) PCT Filed: Jun. 29, 2010

(86) PCT No.: PCT/CN2010/074729
§ 371 (c)(1),
(2), (4) Date: Sep. 13, 2010

(87) PCT Pub. No.: WO2011/000309
PCT Pub. Date: Jan. 6, 2011

(65) Prior Publication Data
US 2011/0152205 A1    Jun. 23, 2011

(30) Foreign Application Priority Data
Jun. 29, 2009   (CN) .......................... 2009 1 0115608

(51) Int. Cl.
*A61K 31/35* (2006.01)
*A61K 31/70* (2006.01)
(52) U.S. Cl. ......................................... 514/456; 514/27
(58) Field of Classification Search ..................... 514/26, 514/27, 456
See application file for complete search history.

(56) References Cited

U.S. PATENT DOCUMENTS
5,783,189 A * 7/1998 Pei et al. .......................... 514/23

FOREIGN PATENT DOCUMENTS
| CN | 1321500 A | 11/2001 |
|---|---|---|
| CN | 1813780 A | 8/2006 |
| CN | 101301303 A | 11/2008 |
| CN | 101627990 A | 1/2010 |

OTHER PUBLICATIONS

Wu et al, "Injection of Chinese herbal extract for chest pain of unstable angina", Published Online: Jan. 21, 2009.*
International Search Report issued Sep. 30, 2010 to international application No. PCT/CN2010/074729.

* cited by examiner

*Primary Examiner* — Elli Peselev
(74) *Attorney, Agent, or Firm* — Knobbe, Martens, Olson & Bear, LLP

(57) ABSTRACT

The invention relates to the new usage of puerarin in the field of pharmaceutical products, in other words, it relates to the application of puerarin in the preparation of drugs for P2X$_3$ mediated pain/nervous system diseases. The experiment shows that puerarin can inhibit pain-related behavioral responses, subsequently immunohistochemical analysis, in situ hybridization, RT-PCR, protein blotting and other techniques were utilized to observe the inhibition of puerarin on mRNA and protein expression of P2X$_3$ receptor in dorsal root ganglion of rats with neuropathic pain and in dorsal root ganglion and sensory nerve ending in the burn model of rats, it was found by using whole-cell patch clamp technique that puerarin can significantly reduce the electric current activated by P2X$_3$ receptor agonist in the neuron of dorsal root ganglion of rats with neuropathic pain. The experiment proves that the mechanism for the inhibitory effects of puerarin on acute and chronic pain is to block the transmission of pain sense information that is mediated by P2X$_3$ receptor in primary sensory neurons. The invention provides a kind of new method for the prevention and treatment on acute and chronic pain, and it also indicates that puerarin can act as a antagonist for P2X$_3$ receptor, which will be helpful for the application of drugs in the prevention and treatment on P2X$_3$ receptor involved nervous system diseases.

2 Claims, 7 Drawing Sheets

Drawings

APPLICATION OF PUERARIN IN THE PREPARATION OF P2X₃ MEDIATED DRUGS FOR PAIN/NERVOUS SYSTEM DISEASES

CROSS-REFERENCE TO RELATED APPLICATIONS

This application is the U.S. National Phase under 35 U.S.C. §371 of International Application PCT/CN2010/074729, filed Jun. 29, 2010, which was published in a non-English language, which claims priority to CN 200910115608.8, filed Jun. 29, 2009.

FIELD OF THE INVENTION

The present invention relates to use of analgesic drug, particularly to the applications of puerarin that can be used in preventing and treating pain in the preparation of $P2X_3$ mediated drugs for pain/nervous system diseases.

BACKGROUND OF INVENTION

Pain is the common symptom of most of the diseases and it is a kind of unpleasant feeling with large individual difference in human. Since pain causes tremendous suffering to people, the $106^{th}$ national congress of USA has passed a resolution and declared the ten years since Jan. 1, 2001 as the Decade of Pain Control and Research according to the report on Volume 2 of "Newsletter of the International Association for the Study Pain" in 2001. Therefore, it can be found that various countries have placed emphasis on the pain research. According to the time course of pain, it can be divided into acute pain (physiological pain) and chronic pain (pathological pain). Wherein, chronic pain includes inflammatory pain, neuropathic pain and cancer pain, which is one of the frequently seen chief complaints in clinical study. Since the mechanism of chronic pain is complex, its treatment has become a difficult problem in clinical study. Neuropathic pain refers to the pain syndrome that is induced by injuries in nervous system or diseases, which is always characterized by spontaneous pain, hyperpathia to mechanical stimulation, cold, heat and other harmful stimulation; allodynia, paralgesia, burn pain and other nervous pathological hyperpathia to non-harmful stimulation. Since the duration of chronic pain is always long and causes relatively big damages to physical and mental health of people, the studies on this topic have become the hot spot and emphasis of pain field. Burn is a kind of serious wound and burn pain is also one of the most serious acute pain, and inflammatory pain may be induced by inflammatory reactions after burn. Pain is often the first reaction of burn patients, different degrees of pain may be found in the wound surface or no significant pain is found at the first hour after burn, and subsequent pain is always affected by the following factors: such as depth of burn, stage for course of disease, therapeutic measures, individual factors of patients and so on. Pain after burn is induced by the stimulation to nociceptor on the skin of injured portion as well as accompanied inflammatory reactions and nerve injuries, therefore, its treatment requires the combination of nociceptive treatment and neuropathic treatment.

Purine adenosine triphosphate (ATP) is involved in pain information transmission as an important messenger substance. Purine receptors can be divided into Purine 1 and Purine 2 (P1,P2) receptor, ATP and its analogs can take effects on P2 receptor. P2 receptor can be divided into ligand gated ion channel receptor (P2X receptor) and G protein coupled receptor (P2Y receptor). P2X receptor has seven kinds of subtypes ($P2X_{1-7}$). It was reported in Nature of the United Kingdom that $P2X_3$ receptor (a subtype of P2X receptor) that reacted with ATP can be specifically cloned and expressed in the neurons in dorsal root ganglion. Pain and noxious stimulation can lead to the release of ATP in large amount by injured cells, stress cells and sensory nerve ending itself. ATP and reactive P2X receptor are involved in the transmission of pain and noxious information in primary sensory neurons, among them homologously polymerized $P2X_3$ receptor is involved in the transmission of pain and noxious information in primary sensory neurons. $P2X_3$ receptor gene knock-out mice reduced the two-phase reaction in formalin pain inducing experiment. $P2X_3$ receptor can mediate the transmission of pain in neuropathic pain. The expression of $P2X_3$ receptor and $P2X_3$mRNA increases during the stimulation in neuropathic pain, sensory neuron $P2X_3$ receptor-mediated ATP-activated electric current via gated channel significant increases. Application of $P2X_3$ receptor anti-sense oligonucleotide and RNA interference technique may down-regulate the level of $P2X_3$ receptor in the dorsal root ganglion of inflammatory pain model of rats, and then significantly alleviate the noxious reaction in footplates that are induced by $P2X_3$ receptor agonist $\alpha,\beta$-meATP and formalin. These findings can provide new evidences for the pathogenesis of neuropathic pain. Previous studies in the laboratory by the applicant have also indicated that burn may lead to the increase in $P2X_3$ receptor expression in the sensory neurons of dorsal root ganglion. Currently, studies have been reported on preparation of $P2X_3$ receptor antagonists (such as RO3) for clinical treatment on pain in other countries.

Pain relieved by chemical drugs is still the most frequently used therapeutic tool on pain now, which mainly includes opioid analgesic, non-opioid analgesic with central effect, anti-inflammatory analgesic with peripheral effect and compound anti-inflammatory analgesic. But the incidence rate of adverse effects such as respiratory depression, nausea, vomit, drowsiness, urinary retention and other symptoms in opioid and other analgesic is relatively high, and long-term application may lead to drug tolerance and dependence as well as withdrawal syndrome that is induced by sudden drug withdrawal. Antifani (Indometacin) is a kind of non-steroid anti-inflammatory drug having antipyretic effects, abirritation and anti-inflammatory effect, and its mechanism is to reduce prostaglandin synthesis by inhibiting epoxidase, prevent the formation of pain nerve impulse in inflammatory tissues and inhibit inflammatory reactions, including chemotropism of leucocytes, release of lysomal enzymes and so on. Since idomethine has several kinds of serious adverse effects, its applicable range is thus affected. Therefore, the exploration of analgesic drug on the basis of new molecular targets has become the hot spot of researches and the most important task now.

Puerarin is a kind of flavonoid glycoside that is extracted from the root of leguminous plant *Pueraria lobata* and *Pueraria thomsonii* Benth., which is mainly used in the treatment on cardiovascular diseases and diabetes. Previous studies have reported that [Zhou Jun, Fang Suping, Qi Yun, et al. Effect of GeGen Decoction on Inflammatory Media in Joint of Adjuvant Arthritis Rats. Chinese Journal of Experimental Traditional Medical Formulae, 2001, 7(3): 29-31.] Puerariae Decoction with pueraria as the major drug has anti-inflammatory action. This study indicates that puerarin that is extracted from pueraria may prevent noxious reactions and affect pain sense, but no result on the direct abirritation of puerarin has been reported, and no report on the treatment on pain by utilizing analgesic effects of puerarin is available in clinical study.

SUMMARY OF THE INVENTION

The first purpose of the present invention is to provide the first new usage of puerarin, namely the application of puerarin in the preparation of drugs for treating chronic pain (preferably neuropathic pain).

The second purpose of the present invention is to provide the second new usage of puerarin, namely the application of puerarin in the preparation of drugs for treating acute pain (preferably burn pain).

The third purpose of the present invention is to provide the third new usage of puerarin, namely the application of puerarin in the preparation of drugs for prevention and treatment involving in the pathological and physiological mechanisms for $P2X_3$ receptor mediated nervous system diseases as a kind of $P2X_3$ purinoceptor antagonist.

Puerarin can alleviate the neuropathic pain (chronic pain) and pain-related behavioral responses of burn rats (acute pain). The mechanism for the treatment of acute pain/chronic pain by using puerarin is to block the pain information transmission mediated by $P2X_3$ receptor and take effects on preventing and treating pain.

In order to get a better understanding over the essence of the present invention, usages of puerarin is further confirmed by the experiments and results referring to the attached figures as below.

DETAILED DESCRIPTION OF THE EMBODIMENTS

Figure 1:
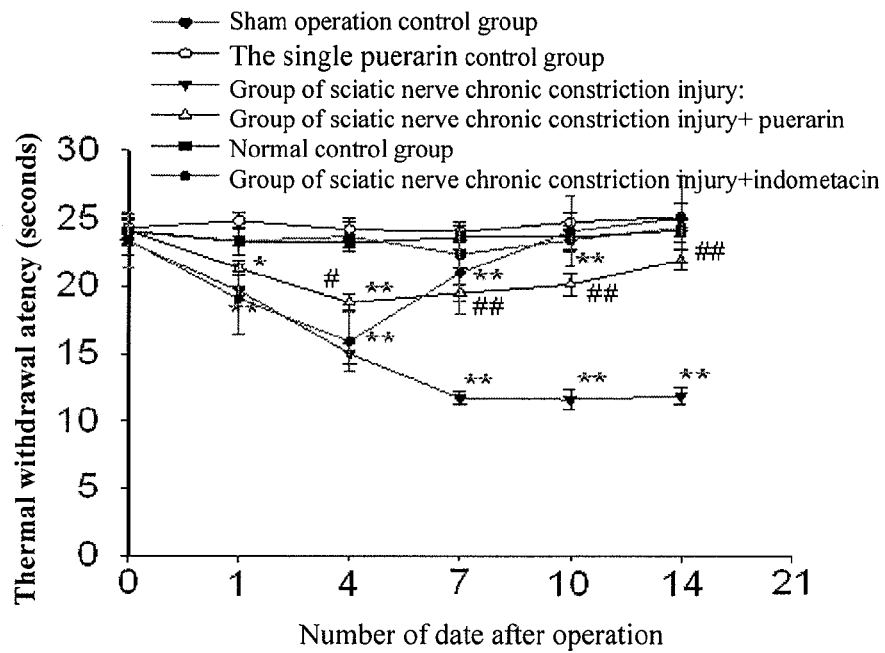
FIG. 1 is a diagram for the effects of puerarin on thermal hyperalgesia of rats that suffer from neuropathic pain.

The present invention is illustrated with the effects of puerarin on neuropathic pain (the representative of chronic pain) and burn pain (the representative of acute pain) as the examples.

1. Materials and Methods (I) Research on the Effects of Puerarin on $P2X_3$ Receptor Mediated Neuropathic Pain 1.1 Animals and Grouping:

Male SD rats, 220-250 g were provided by the Department of Experimental Animals from the Medical College of Nanchang University. The rats were divided into five groups at random and 12 rats were included in each group. Experimental grouping: I (sham); II (puerarin); III (chronic constriction injuries, CCI); IV (CCI+puerarin); V (control); VI (CCI+Indo). The puerarin injection was dissolved in physiological saline and the concentration was 50 mg/mL. Group I were subjected to intraperitoneal injection of physiological saline (4 mL/kg); Group II were subjected to intraperitoneal injection of puerarin injection (4 mL/kg); Skins of the Group III (the sham operation group) were cut open and their sciatic nerves were exposed, then their skin was sew up without ligating nerves. Group IV were subjected to intraperitoneal injection of puerarin injection (4 mL/kg) everyday on the first day after CCI operation. Intraperitoneal injection of idomethine (4 mg/kg/d) was carried out on the rats in group IV half an hour before the operation and after the operation everyday, and the injection was carried out once a day until the test was finished.

1.2 Drugs and Reagents:

Puerarin, which was produced by Shandong Fangming Pharmaceutical Stock Co. Ltd. (production number: 0804171); Thiopental sodium, which was produced by Shanghai New Asiatic Pharmaceuticals Co. Ltd. (production number: 050101); SP kit, in-situ hybridization kit and DAB kit (Beijing Zhongshan Biotechnology Co. Ltd.); $P2X_3$ antibody was purchased from Chemicon International Inc. in USA. Adenosine 5-triphophate (ATP) from sigma, which was prepared with DRG extracellular fluid, pH7.4. $\alpha$, $\beta$-methylene ATP ($\alpha,\beta$-meATP) from sigma, which was prepared with DRG extracellular fluid, pH7.4. Trinitro-adenosine triphosphate (TNP-ATP) from sigma, which was prepared with DRG extracellular fluid, pH7.4. The ingredients of tnternal solution for capillary glass microelectrode include (mmol·L-1): KCl 140, $CaCl_2$ 1, $MgCl_2$ 2, HEPES 10, EGTA 11, ATP 4. Electric resistance of the electrode 2~5MΩ. The ingredients of DRG extracellular fluid for perfusion (external solution) include (mmol·L-1): NaCl 150, KCl 5, $CaCl_2$ 2.5, $MgCl_2$ 1, HEPES 10, D-Glucose 10.

1.3 Major Equipments:

BME-403 Von Frey fine thread (Institute of Biomedical Engineering, Chinese Academy of Medical Sciences); BME-410C type automatic thermalgia stimulator (Institute of Biomedical Engineering, Chinese Academy of Medical Sciences); antiseptic gauze, towel, cotton swab and so on, iodine tincture, 75% ethanol, operation instrument set: scissors, small ophthalmological pincett, vascular forceps, silk suture, toothed forceps, nerve dissector and others.

Experimental devices for patch clamp and related accessories: CEZ-2400 type whole-cell patch clamp amplifier (Nihon-Kohden, Japan), SBR-I type second-line oscillometer (Shantou Ultrasound Electronic Instrument Factory), 95-B capillary glass microelectrode puller (Laboratory of Molecular and Cellular Neurobiology, Tongji Medical College, Huazhong University of Science and Technology), analytical balance (Shanghai Balance Instrument Factory), stimulator (SEN-7203, Nihon-Kohden, Japan), isolator (SS-202J, Nihon-Kohden, Japan), LMS-2B type two-way electrophysiolograph (Chengdu Instrument Factory), capillary glass microelectrode (GG-17, Instrument Repairing and Production Factory, West China University of Medical Science), inverted microscope (Olympus, Japan), HY-Z adjustable multiple-use constant temperature shaker (Guohua Electrical Apparatus Co. Ltd).

1.4 Preparation of Chronic Neuropathic Pain Model:

Thiopental sodium was used to anesthetize the rats (30 mg/kg, intraperitoneal injection), and the skin in the outer side of right thighs of the rats was cut open under sterile conditions, and blunt dissection was carried out to isolate the sciatic nerves, then the sciatic nerves were slightly ligated with 4-0 chromicized catgut and four ligations were carried out in total, and an interval of about 1 mm was left between two knots. It can be seen during the ligation that the ligated positions in sciatic nerves slightly reduced and transient tic in right posterior limb can be found, it should be paid attention not to ligate too tight in case of completely block peripheral blood flow in the nerves. The rats were raised in separate cages after the operation, and mechanical withdrawal threshold and thermal withdrawal latency were determined before the operation (0 d) and 1, 3, 5, 7, 9, 11, 14 days after the operations respectively (Time for the determination is set at 10□00-14□100 everyday, and the room temperature was maintained at 22±0.5° C.).

1.5 Detection on Mechanical Hyperalgesia in Rats that Suffer from Neuropathic Pain:

BME-403 Von Frey fine thread (Institute of Biomedical Engineering, Chinese Academy of Medical Sciences) was used to determine the mechanical withdrawal threshold (MWT). The rats were kept in transparent organic glass box (22×12×22 $cm^3$), and the bottom of the organic glass box was made of wire netting of 1×1 $cm^2$. The rats were raised in the laboratory after operations and they were kept in the organic glass box for accommodation for 15 min before the detection. The bending forces were 0.13, 0.20, 0.33, 0.60, 1.30, 3.60, 5.00, 7.30, 9.90, 20.1 g respectively, and bending forces≧20.1 g were recorded as 20.1 g. Each test was performed for ten times from the smallest bending force until the frequency of withdrawal was higher than 5/10, namely 50% reaction threshold (that was the value for inducing five reactions in ten tests. The test was repeated for three times and the average was used). The interval between two stimulations was at least more than 15 s until the stimulation-induced reactions (such as licking feet and throwing legs) completely disappeared.

1.6 Detection on Thermal Hyperalgesia in Rats that Suffer from Neuropathic Pain:

The organic glass box was placed on a glass plate of 3 mm thick and BME-410C type automatic thermalgia stimulator (Institute of Biomedical Engineering, Chinese Academy of Medical Sciences) was used to irradiate the footplates of rats. The time for the appearance of leg withdrawal after the irradiation on footplates of rats by using the thermal radiation stimulator was considered as the thermal withdrawal latency (TWL). The time for cutting off was 30 seconds in order to prevent burn on tissues.

1.7 $P2X_3$ Receptor Expression in Dorsal Root Ganglion (DRG) of Rats:

The five groups of rats were subjected to intraperitoneal injection of Thiopental sodium (30 mg/kg) for deep anesthesia on the $14^{th}$ day after the operation, and intra-arterial infusion of 4% paraformaldehyde (0.1 mol/L PB, pH7.4) via ascending aorta was carried out. L4 and L5 sections of DRG were isolated from the rats and then fixed in 4% paraformaldehyde/0.1 m PBS (containing 0.1% DEPC) for 2 hours, then they were subjected to dehydration with 20% sucrose. Frozen sectioning was carried out on a cryostat microtome, the thickness was 15 μm. The samples were stored in 4% paraformaldehyde. A section was selected from every five DRG sections from each rat for the two-step immunohistochemical staining to detect the expression of $P2X_3$ receptor in DRG neurons and DAB coloration. At the same time, in situ hybridization on DRG sections was carried out to detect the expression of $P2X_3$ receptor mRNA, after all of the liquids and containers for hybridization were strictly handled with 0.1% DEPC. The frozen sections were kept in 0.05% $H_2O_2$ at room temperature for 30 minutes in order to remove the endogenous peroxydase and they were digested with pepsin for 1-2 minutes, then incubated in prehybridization solution at 37° C. for 2 hours. Subsequently, the prehybridization solution was discarded and the sections were transferred to the hybridization solution in a water bath at 37° C. over night. On the next day, gradient saline sodium citrate solutions (2×SSC, 0.5×SSC and 0.2×SSC) were used to rinse the sections for 15 minutes respectively. Then the sections were transferred to the blocking buffer at 37° C. for 30 minutes and then in biotinylated digoxin at 37° C. for 30 minutes. They were rinsed with 0.05% PBS for 15 minutes and then incubated in SABC-POD and biotinylated peroxydase for 30 minutes respectively, and subsequently they were subjected to DAB coloration. The results were analyzed by using the image analysis system software (Wuhan Tianping Image Technological Co. Ltd., HMIAS-2000 high-resolution color medical image analysis system) on the average optical density value of $P2X_3$ positive neurons.

1.8 The Effects of Puerarin on ATP or $\alpha,\beta$-meATP Activated Electric Current in DRG Neurons in CCI Rats:

1.8.1 Specimen Preparation:

The method for neuron sample isolated from DRG of rats was briefly described as below: the rats were knocked down and their skin in the back was cut open rapidly after decollation. The ribs that were connected to the spinal column at both sides were cut apart and the thoracolumbar spine was taken out and cut in half through the middle of the spine. The samples were kept in $O_2$ saturated DMEM solution (Dubecco's Modified Eagle's medium), pH 7.40, and the osmotic pressure of this solution was 340 mOsm/kg. The sections L4 and L5 of nerve ganglion and connected nerve roots (dorsal nerve roots and ventral roots) as well as the spinal nerves were taken out inside the open vertebral canal, the connected nerves and adjacent connective tissue capsule were carefully removed by using fine corneal scissors and hairspring tweezer under an anatomical microscope, and the cleaned DRG should be cut into small pieces as far as possible and transferred to a culture flask, trypsin (type III, sigma) 0.5 g/L and collagenase (type IA, sigma) 1.0 g/L was then added, and the culture flask was incubated in a constant temperature shaking water bath (35□, 80 times/min) for 20-30 minutes, then proper amount of Soya beam trypsin inhibitor (type □-s, Sigma) was added to stop the enzymatic digestion. The DRG cells after the above mentioned enzymatic and mechanical isolation were transferred to 35 mm culture dishes, and then they were kept still on the object stage of an inverted microscope for solution change for 30 minutes, subsequently the whole-cell patch clamp technique was utilized to record the effects of puerarin on ATP or $\alpha,\beta$-meATP activated electric current.

1.8.2 Operation Procedures for the Whole-Cell Patch Clamp Test:

(1) Carefully examining the connection and original setting of equipments in the experimental system.

(2) Turning on the power switch.

(3) Electrode installation: connecting the reference electrode, filling the glass electrode and then installing it on the electrode clamp holder. Notice: the electrode should not be over-filled; contacting the shielding can with hands before installing the electrodes in order to release the static electricity on the body.

(4) Phase boundary potential compensation and electrode resistance determination: filling solution in the microelectrode under the "searching" mode, adjusting the phase boundary potential compensation and measuring electrode resistance according to the responsive amplitude of electric current that was induced by pulsed voltage square wave.

(5) Cell sealing: adjusting the micro-operator to get the tip of the microelectrode close to the surface of the cell and a negative pressure is produced in the micro-electrode and thus the Giga-Ohm seal was formed.

(6) Rapid electric capacity compensation: adjusting the rapid electric capacity compensation and making the output signal free of ingredients of rapid electric capacitive current.

(7) Absorbing the cell membrane until it was disrupted: the working mode was switched to "forcipressure". The membrane was absorbed until it was disrupted after the high resistance sealing was formed between the electrode and the cell (1-10 G$\Omega$). The holding potential (H.P) was kept at −60 mV, and low pass membrane current was used (1 kHz, −3 dB).

(8) Slow capacitive compensation: adjusting the slow capacitive compensation and making the output signal free of ingredients of slow electric capacitive current. Tandem resistance compensation: adjusting the tandem resistance compensation until no shock was produced.

The equipment for record of patch clamp was CEZ-2400 type patch clamp amplifier (Nihon-Kohden, Japan). The membrane was further absorbed until it was disrupted after the high resistance formed between the electrode and the cell membrane (1~10 G$\Omega$), and the capacitance and the tandem resistance compensation were adjusted. The holding potential (HP) was kept at −60 mV, low pass membrane current was used (1 kHz, −3 dB). The experimental results were traced by using the two-way recorder (LMS-2B, Chengdu). ATP concentration-effect curve was plotted according to the formula as below: $I=Imax/[1+(EC_{50}/C)n]$. In this formula, C was the concentration of ATP, I was the ATP activated electric current after standardization, Imax was the maximal value of ATP activated electric current after standardization, $EC_{50}$ or Kd was the 50% effective concentration for ATP to take the largest effect, n was Hill coefficient. The drug medication was carried out by moving the releasing tube of the rapid drug changing device with the micro-operator, the diameter of each tube was 0.2 mm, and the entrance of the tube was about 100 µm from the detected cell. The intracellular drug dialysis during the experiment was carried out by introducing drugs via the microtubule in the glass microelectrode. The experiment was carried out at room temperature between 20~30° C.

1.9 Statistical Processing for Experimental Data:

Data from different groups were represented by x±sem. One-way ANOVA was carried out for the comparisons between groups, and paired comparison was carried out by using the least significant difference (LSD). SPSS11.0 software package was used for the data processing. $P<0.05$ indicated that the difference was significant.

(II) Research on the Effects of Puerarin on $P2X_3$ Receptor Mediated Burn Pain 2.1 Animals and Grouping:

Male SD rats, 220-250 g, 60 rats were included, which were provided by the Department of Experimental Animals from the Medical College of Nanchang University, and the animals were divided into different groups at random. Group I was the group of sham burn in skin of feet; group II was the group of puerarin injection+first degree or superficial second degree burn in skin of feet; group III was the group of physiological saline+first degree or superficial second degree burn in skin of feet; group IV was the group of sham burn in skin of back; group V was the group of puerarin injection+first degree or superficial second degree burn in skin of back; group VI was the group of physiological saline+first degree or superficial second degree burn in skin of back. Puerarin injection was dissolved in physiological saline and the concentration was 50 mg/mL. vena caudalis injection of 4 mL/kg physiological saline was carried out for the rats in group III and group IV 0.5 h before burn, and the injection was carried out once a day until the termination of the test; group II and group V were subjected to vena caudalis injection of 4 mL/kg puerarin injection 0.5 h before burn, and the injection was carried out once a day until the termination of the test; skin of feet or back of the rats from group I and group IV (the sham burn group) were immersed in warm water of 37° C. for 8 seconds.

2.2 Drugs and Reagents:

Puerarin, which was produced by Shandong Fangming Pharmaceutical Stock Co. Ltd. (production number:

0804171); ether, Tianjin Damao Chemical Reagent Factory (production number: 050801); thiopental sodium, which was produced by Shanghai New Asiatic Pharmaceutical Co. Ltd. (production number: 050101); SP kit, DAB kit (Beijing Zhongshan Biotechnology Co. Ltd); $P2X_3$ antibody (Chemicon International Inc., USA); S100 antibody (Wuhan Boster Company).

2.3 Major Equipments:

BME-403 Von Frey fine thread (Institute of Biomedical Engineering, Chinese. Academy of Medical Sciences); BME-410C type automatic thermalgia stimulator (Institute of Biomedical Engineering, Chinese Academy of Medical Sciences); patch clamp and related accessories: CEZ-2400 type whole-cell patch clamp amplifier (Nihon-Kohden, Japan), SBR-I type two line oscillograph (Shantou Ultrasound Electronic Instrument Factory), 95-B capillary glass microelectrode puller (Laboratory of Molecular and Cellular Neurobiology, Tongji Medical College, Huazhong University of Science and Technology, analytic balance (Shanghai Balance Instrument Factory), stimulator (SEN-7203, Nihon-Kohden, Japan), isolator (SS-202J, Nihon-Kohden, Japan), LMS-2B type two-way electrophysiograph (Chengdu Instrument Factory), capillary glass microelectrode (GG-17, Instrument Repairing and Production Factory, West China University of Medical Science), inverted microscope (Olympus, Japan), HY-Z adjustable multiple-use constant temperature shaker (Guohua Electrical Apparatus Co. Ltd).

2.4 Preparation and Determination of Burn Model 2.4.1 Preparation of Burn Model:

2.4.1.1 Superficial Second Degree Burn Model in Feet of Rats:

After the rats were anesthetized by ether, their right posterior feet were immersed in hot water of 70° C. for 5 seconds or 8 seconds, then they were raised in separate cages after burn. The mechanical withdrawal threshold and the thermal withdrawal threshold in their right posterior feet were measured respectively before burn (Oh) and 1, 24, 48, 72, 96, 120, 144 hours after burn (the room temperature was maintained at 22±0.5° C.).

2.4.1.2 Superficial Second Degree Burn Model in Back of Rats:

After the rats were anesthetized by ether, their fur on the skin of back was removed and then they were immersed in water of 70° C. for 5 seconds or 8 seconds, the burn area was about 30% to form superficial second degree burn model in back of rats, and then they were raised in separate cages after burn. The wound surfaces were exposed without treatment.

2.4.2 Determination of First Degree and Superficial Second Degree Burn Rats:

After the skin of rats that suffered from first degree burn was immersed into water of 70° C. for 5 seconds, red spots and slight edema can be seen after about 15 minutes, and HE staining on the pathological sections showed that it was first degree burn. After the skin of rats that suffered from superficial second degree burn was immersed into water of 70° C. for 5 seconds, red spots and slight edema can be seen after about 15 minutes, and blister can be found after 3 hours, HE staining on the pathological sections showed that it was superficial second degree burn. No significant infection was found in the rats that suffered from burn before they were killed.

2.5 Detection on Mechanical Hyperalgesia in Rats that Suffered from Foot Burn:

BME-403 Von Frey fine thread was used to detect the mechanical withdrawal threshold (MWT). The rats were kept in transparent organic glass box (22×12×22 $cm^3$), and the bottom of the organic glass box was made of wire netting of 1×1 $cm^2$. The rats were raised in the laboratory after operations and they were kept in the organic glass box for accommodation for 15 min before the detection. The bending forces were 0.13, 0.20, 0.33, 0.60, 1.30, 3.60, 5.00, 7.30, 9.90, 20.1 g respectively. Each test was performed for ten times from the smallest bending force until the frequency of withdrawal was higher than 5/10, namely 50% reaction threshold (that was the value for inducing five reactions in ten tests). The biggest bending force was 20.1 g and bending forces≧20.1 g were recorded as 20.1 g. The interval between two stimulations was at least more than 15 seconds until the stimulation-induced reactions (such as licking feet and throwing legs) completely disappeared.

2.6 Detection on Thermal Hyperalgesia in Rats that Suffered from Foot Burn:

The organic glass box was placed on a glass plate of 3 mm thick and BME-410C type automatic thermalgia stimulator was used to irradiate the footplates of rats. The time for the appearance of leg withdrawal after the irradiation on footplates of rats by using the thermal radiation stimulator was considered as the thermal withdrawal latency (TWL). The time for cutting off was 25 seconds in order to prevent burn on tissues.

2.7 Test on $P2X_3$ Receptor Expression in Nerve Ending in the Skin of Rats that Suffered From Back Burn:

Intravenous injection of puerarin or physiological saline (5 mL/kg) via tail vena was carried out everyday for continuous three days on the rats that suffered from burn, then the rats in different groups were subjected to intraperitoneal injection of thiopental sodium (30 mg/kg) for deep anesthesia. The burn skin on the back of the rats was cut off (about 1.5-2 $cm^2$ in size), then was fixed and subjected to paraffin imbedding. The thickness of the intersectional sections for immunohistochemical analysis was 4 μm. The sections were subjected to two-step immunohistochemical staining and DAB coloration. Two continuous sections were selected from every five sections of skin for each rat, among them one section was used for the detection of $P2X_3$ receptor expression in nerve ending in the skin, and the other section was used for the detection of S100 expression in nerve ending in the skin. The results were analyzed by using the image analysis system software (Wuhan Tianping Image Technological Co. Ltd. HMIAS-2000 high-resolution color medical image analysis system) on the average optical density value of $P2X_3$ positive neurons.

2.8 Statistical Processing of Experimental Data:

Data from different groups were represented by x±sem. One-way ANOVA was carried out for the comparisons between groups, and paired comparison was carried out by using the least significant difference (LSD). SPSS11.0 software package was used for the data processing. P<0.05 indicated that the difference was significant.

2. Results (I) Results for the Effects of Puerarin on $P2X_3$ Receptor Mediated Neuropathic Pain No dyskinesia or self-mutilation was found in the rats in different groups after operations.

1.1 Ethological Research:

1.1.1 Detection on Thermal Hyperalgesia of the Rats that Suffered from Neuropathic Pain:

The model of neuropathic pain was basically formed after the sciatic nerve was ligated for four days, the thermal withdrawal latency (TWL) in the group III (chronic constriction injury, CCI) and the group IV (CCI+puerarin) and the group VI (CCI+Indocin) significantly decreased in comparison to those of the group I (sham), the group II (puerarin) and the group V (control) (p<0.01), while the difference in the comparisons between group I (sham), the group II (puerarin) and the group V (control) was not significant (p>0.05). The thermal withdrawal latency (TWL) in the group IV (CCI+puerarin) significantly decreased in comparison to those of the group I (sham), the group II (puerarin) and the group V (control) (p<0.01), but the difference in the comparison with the group III (CCI) significantly increased (p<0.01). The difference in the comparison in the thermal withdrawal latency between the group IV (CCI+puerarin) and the group V (control) after 14 days was not statistically significant (p>0.05), while the thermal withdrawal latency in the group III (CCI) was still low (p<0.01). Seven days after the sciatic nerve was ligated, the thermal withdrawal latency in the group VI (CCI+Indocin) increased in comparison to that of CCI and the difference was significant (p<0.01), and the difference in the comparison with the group IV was not significant (p>0.05). (see FIG. 1).

Figure 2:
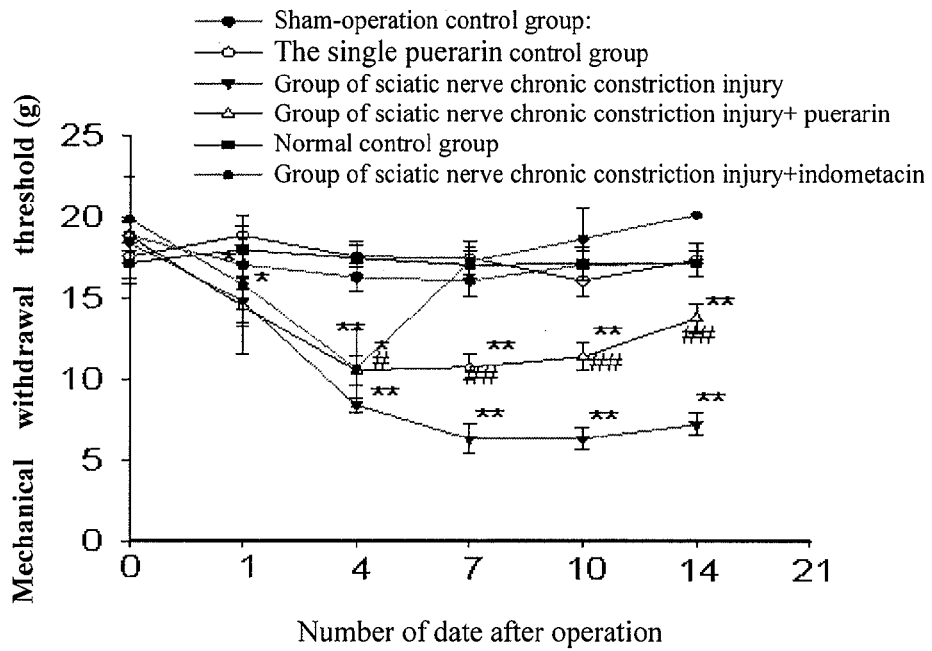
FIG. 2 is a diagram for the effects of puerarin on mechanical hyperalgesia of rats that suffer from neuropathic pain.

1.1.2 Detection of Mechanical Hyperalgesia of the Rats that Suffered from Neuropathic Pain:

The model of neuropathic pain was basically formed after the sciatic nerve was ligated for four days, the mechanical withdrawal threshold (MWT) in the group III (chronic constriction injury, CCI), the group IV (CCI+puerarin), and the group VI (CCI+Indocin) significantly decreased in comparison to those of the group I (sham), the group II (puerarin) and the group V (control) (p<0.01), while the difference in the comparison between the group I (sham), the group II (puerarin) and the group V (control) was not significant (p>0.05). Seven days after the sciatic nerve was ligated, though the mechanical withdrawal threshold (MWT) in the group IV (CCI+puerarin) was still low (p<0.01) in comparison to that of the group V (control), the mechanical withdrawal threshold (MWT) in the group III (CCI) was even lower in comparison to that of the group V (control) (p<0.01), while the mechanical withdrawal threshold (MWT) in the group IV (CCI+puerarin) significantly increased in comparison to that of the group III (CCI) (p<0.01). After the sciatic nerve was ligated for 7 days, the mechanical withdrawal threshold (MWT) in the group IV (CCI+puerarin) significantly increased in comparison to that of the group CCI (p<0.01), but the difference in the comparison with the group IV was not significant (p>0.05). (see FIG. 2)

Figure 3:
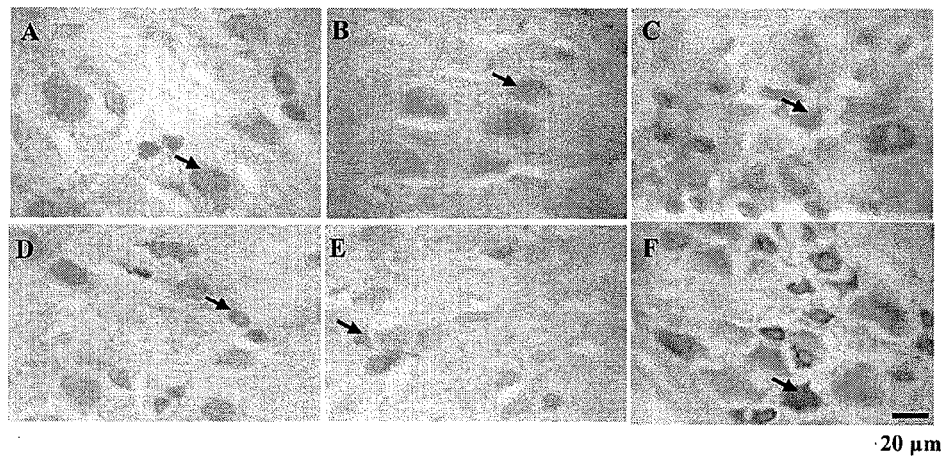
FIG. 3 are the pictures for the effects of puerarin on immunoreactivity of $P2X_3$ receptor in dorsal root ganglion of rats that suffer from neuropathic pain, wherein A: the sham operation group; B: the single puerarin group; C: the group of chronic constriction injuries on sciatic nerve; D: the group of chronic constriction injuries on sciatic nerve+puerarin treatment; E: the normal group; F: the group of chronic constriction injuries on sciatic nerve+idomethine treatment.

1.1.3 Change of the Expression of $P2X_3$ Receptor in Dorsal Root Ganglion (DRG) of Rats:

The expression of $P2X_3$ receptor in dorsal root ganglion in $L_4$ and $L_5$ sections in rats was detected by using immunohistochemical method 14 days after operation. A section was selected from every five sections in $L_4$ and $L_5$ sections of dorsal root ganglion in each rat, and the image analysis system software was used to analyze the change in gray scale of $P2X_3$ positive neurons. The average optical density values of the group I (sham), the group II (puerarin), the group III (CCI), the group IV (CCI+puerarin), the group V (control) and the group VI (CCI+Indocin) were 1.18±0.03, 1.07±0.03, 1.64±0.05, 1.28±0.04, 1.15±0.03 and 1.34±0.04 respectively. The differences in the comparison in $P2X_3$ receptor expression among the group I, the group II and the group V were not significant (p>0.05); the expression of $P2X_3$ receptor in DRG of the group III significantly increased in comparison to those of the group I, the group II and the group V (p<0.01); $P2X_3$ receptor expression in DRG of the group IV was higher than those of the group I, the group II and the group V (p<0.05), but it was still low in comparison to that of the group III (p<0.05); $P2X_3$ receptor expression in the group VI (CCI+Indocin) significantly decreased in comparison to that of the group CCI (p<0.01), $P2X_3$ receptor expression in DRG of the group VI significantly increased in comparison to those of the group I, the group II and the group V (p<0.01), but it was slightly higher in comparison to that of the group V (p<0.05). (see FIG. 3).

Figure 4:
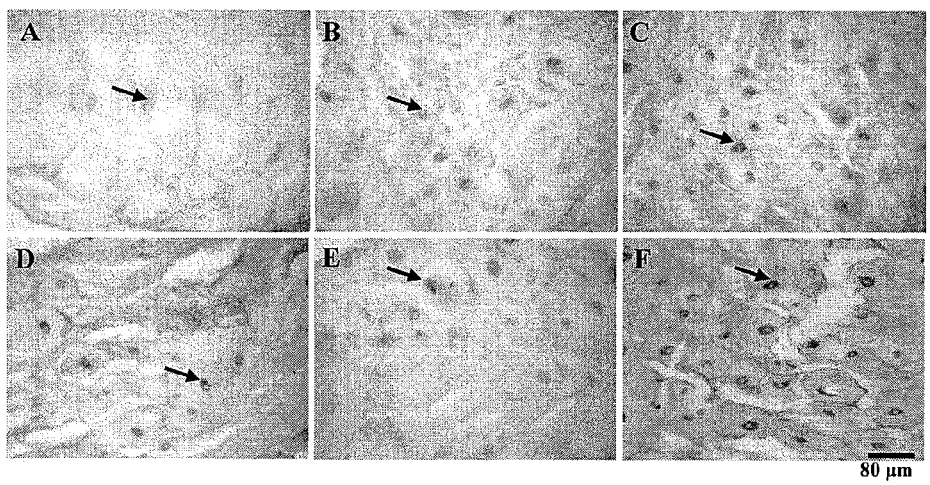
FIG. 4 are the pictures for the effects of puerarin on mRNA expression of $P2X_3$ receptor in dorsal root ganglion of rats that suffer from neuropathic pain, wherein A: the sham operation group; B: the single puerarin group; C: the group of chronic constriction injuries on sciatic nerve; D: the group of chronic constriction injuries on sciatic nerve+puerarin treatment; E: the normal group; F: the group of chronic constriction injuries on sciatic nerve+idomethine treatment.

1.1.4 Change of mRNA Expression of $P2X_3$ Receptor in Dorsal Root Ganglion (DRG) of Rats:

In situ hybridization was used to detect mRNA expression of $P2X_3$ receptor in $L_4$ and $L_5$ sections in dorsal root ganglion (DRG) of rats 14 days after operations. A section was selected from every five sections in $L_4$ and $L_5$ sections in dorsal root ganglion of each rat, and the image analysis system software was used to analyze the change in gray scale of $P2X_3$ positive neurons. Similar to the results from immunohistochemical analysis, the average optical density values of the group I (sham), the group II (Puerarin), the group III (CCI), the group IV (CCI+puerarin), the group V (control) and the group VI (CCI+Indocin) were 0.84±0.01, 0.82±0.03, 1.33±0.02, 0.98±0.05, 0.82±0.02 and 1.14±0.01 respectively. No significant difference was found in mRNA expression of $P2X_3$ receptor among the group I, the group II, the group IV and the group V (p>0.05); mRNA expression of $P2X_3$ receptor in DRG of the group III significantly increased in comparison to those of the group I, the group II and the group V (p<0.01); mRNA expression of $P2X_3$ receptor in DRG of the group IV was significantly higher than that of the group V (p<0.05); mRNA expression of $P2X_3$ receptor in DRG of the group IV was lower than that of the group III (p<0.05), but it was higher than those of the group I, the group II, the group IV and the group V (p<0.05). (see FIG. 4).

1.1.5 Effects of Puerarin on ATP or α,β-meATP Activated Electric Current in DRG Neurons of Rats:

The experiment was carried out in right DRG cells (L4/L5 sections) that were freshly isolated from rats in different experimental groups. The isolated cells were round or oval-shape, and the diameter of these cells was between 25-40 vim. Curled residual roots of axon can be found at one side of most of the cells.

Figure 5:
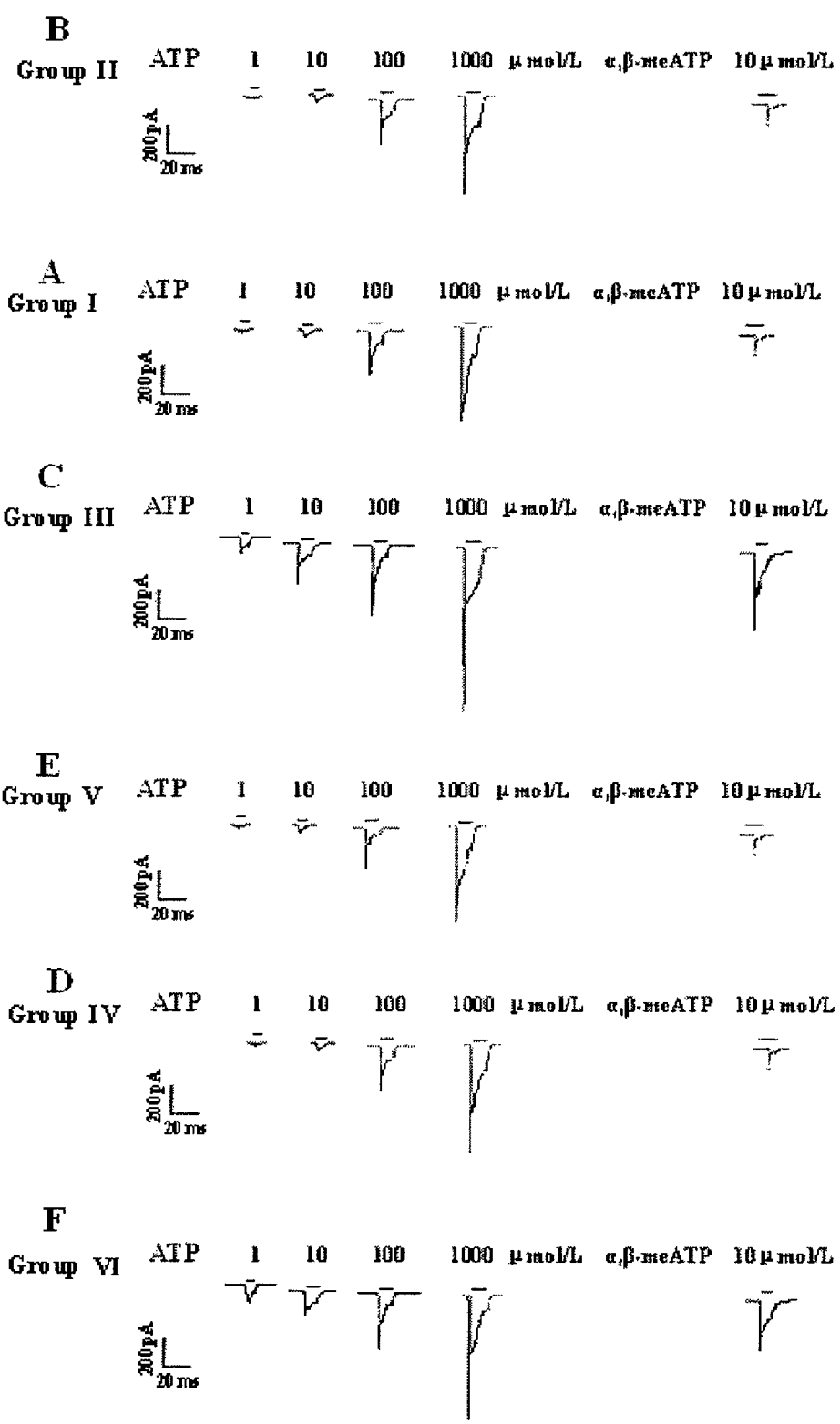
FIG. 5 are the pictures for P2X receptor agonist-activated current in DRG neurons in rats from different groups, wherein A: the sham operation group; B: the single puerarin group; C: the group of chronic constriction injuries on sciatic nerve; D: the group of chronic constriction injuries on sciatic nerve+puerarin treatment; E: the normal group; F: the group of chronic constriction injuries on sciatic nerve+idomethine treatment.

The experiment was divided into the group I (sham), the group II (puerarin), the group III (CCI), the group IV (CCI+puerarin), the group V (control) and the group VI (CCI+Indocin). 36 cells from the group I, 37 cells from the group II, 39 cells from the group III, 40 cells from the group IV and 38 cells from the group V were detected in the experiment, among them 88.9% of group I (32/36), 89.2% of group II (33/37), 87.2% of group III (34/39), 87.5% of group IV (35/40), 86.8% of group V (33/38) and 89.7% of group VI was (35/39) in DRG neurons were sensitive to exogenous ATP (1-1000 μmol/L). ATP-activated electric current ($I_{ATP}$) showed two kinds of inward current (i.e. rapidly desensitized and slowly desensitized current) (though the agonist continuously existed and its concentration did not change, the amplitude gradually decreased and then maintained at a stable value after the activated electric current reached the peak). The completely recovered time for $I_{ATP}$ in the six groups of DRG neurons was about 4-6 min, but $I_{ATP}$ that was produced by DRG neurons in CCI group significantly increased in comparison to those of the other four groups to the same concentration of ATP, and the increase in ATP activated electric current was even significant with the increase in ATP concentration (P<0.05), and no significant difference was found in the comparison among the other four groups (p>0.05). The electric current in the CCI+Indocin group decreased in comparison to that of CCI group (p<0.05); the electric current in CCI+Indocin group was higher than that of the CCI+puerarin group and the difference was significant (p<0.05); $P2X_3$ receptor agonist α,β-meATP (10 μmol/L)-activated electric current produced extremely low inward current in the group I, the group II, the group IV, the group V and the group VI, while an obvious desensitized inward current can be found in the CCI group (p<0.01). The effects of ATP activated electric current in DRG neurons from different groups also showed that ATP activated electric current in DRG nerve cells in neuropathic pain rats significantly increased in comparison to those of the group I, the group II, the group V and the group VI, though the current in the CCI model rats from the drug medication group with puerarin increased in comparison to those of the group I, the group II and the group V, the difference was not significant (p>0.05), and it was lower in comparison to the idomethine treatment group (p<0.05) (see FIG. 5).

Figure 6:
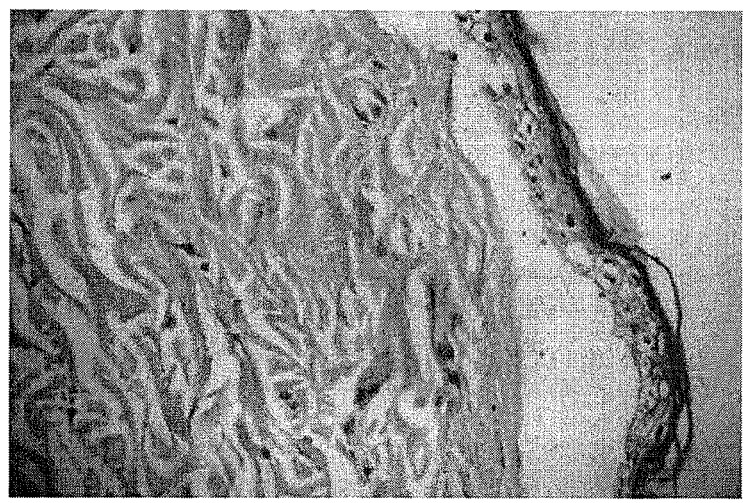
FIG. 6 is the schematic diagram for HE staining of superficial second degree burn skin×40.

(II) Results for the Effects of Puerarin on $P2X_3$ Receptor Mediated Burn Pain 2.1.1 Determination of Rats that Suffered from Superficial Second Degree Burn:

After the rats that suffered from superficial degree second burn were immersed in water of 70° C. for 8 seconds, red spots and slight edema can be found after about 15 minutes, and blister can be found after 3 hours, HE staining on the pathological sections showed that it was superficial second degree burn (see FIG. 6). No significant infection was found in the rats that suffered from burn before they were killed.

Figure 7:
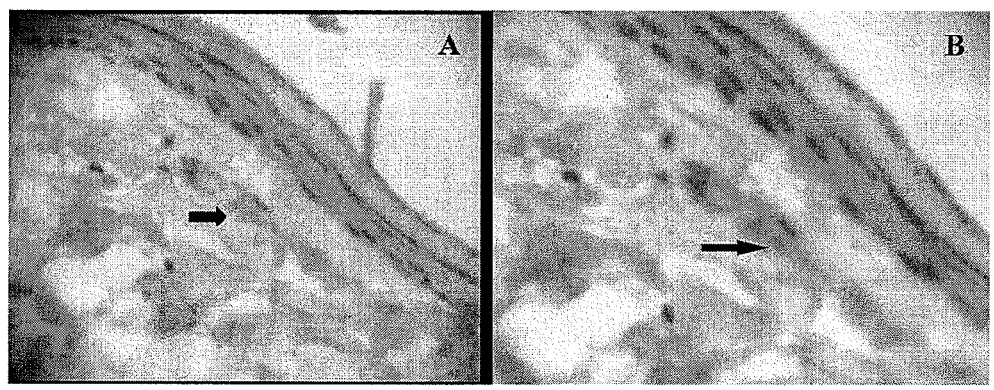
FIG. 7 are the immunohistochemical images for serial sections S-100 and $P2X_3$ of skin specimen, wherein, A is the image for immunologically positive expression of nerve ending S-100; B is the image for immunologically positive expression of nerve ending $P2X_3$, arrows indicate immunologically positive nerve endings.
Figure 8:
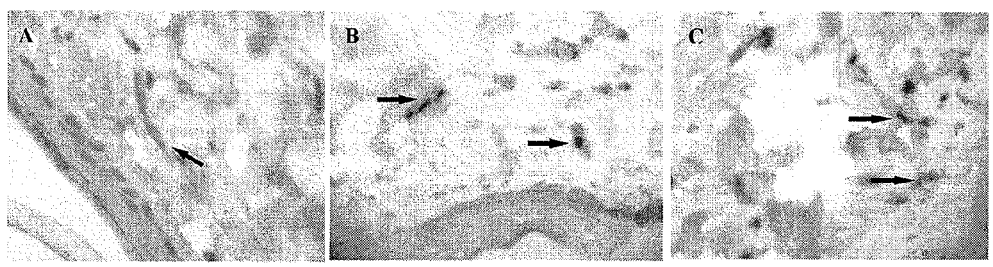
FIG. 8 are the images for the immunohistochemical analysis on $P2X_3$ receptor expression in nerve ending of skin in rats that suffer from burn, wherein A is the group of sham burn in skin of back; B is the group of puerarin injection+superficial second degree burn in skin of back; C is the group of physiological saline+superficial second degree burn in skin of back, arrows indicate positive nerve endings in the immunohistochemical analysis.

2.1.2 Change in $P2X_3$ Receptor Expression in Nerve Ending of Skin in the Rats that Suffered from Burn:

Two-step method was used for the immunohistochemical analysis on nerve ending of skin, and the continuous sectioning showed that the positive nerve ending in S-100 coloration also showed positive expression of $P2X_3$. It can be found under the microscope that the nerve endings of hypodermis in the skin were mainly distributed in the papillary layer nearby the epidermis. They were distributed diffusively nearby hair follicles or glands, see FIG. 7. The image analysis software was used to analyze the average optical density value for immunologically positive nerve ending in the skin. The results showed that the gray scale values in the sham burn group in the back, the group of puerarin injection and superficial second degree burn in the back and the group of physiological saline and superficial second degree in the back were 118.76±18.48, 130.42±13.35 and 152.63±22.62 respectively. After the rats in the group of physiological saline and superficial second degree burn in the back were burned, $P2X_3$ expression in the nerve ending of skin significantly increased, and the difference was significant in comparison to that of the sham burn group in the skin of back (p<0.05), though $P2X_3$ expression in the group of puerarin injection and superficial second degree burn in the back was higher than that of the sham burn group in the skin of back, it was significantly lower than that of the group of physiological saline and superficial second degree burn in the back (p<0.05), indicating that puerarin can reduce the increase in $P2X_3$ expression in the nerve ending of burned skin (see FIG. 8).

2.1.3 Detection on Thermal Hyperalgesia in Rats that Suffer from Foot Burn:

The organic glass box was placed on a glass plate of 3 mm thick and BME-410C type automatic thermalgia stimulator (Institute of Biomedical Engineering, Chinese Academy of Medical Sciences) was used to irrdiate the footplates of rats. The time for the appearance of leg withdrawal after the irradiation on footplates of rats by using the thermal radiation stimulator was considered as the thermal withdrawal latency. The time for cutting off was 30 seconds in order to prevent burn on tissues.

Figure 9:
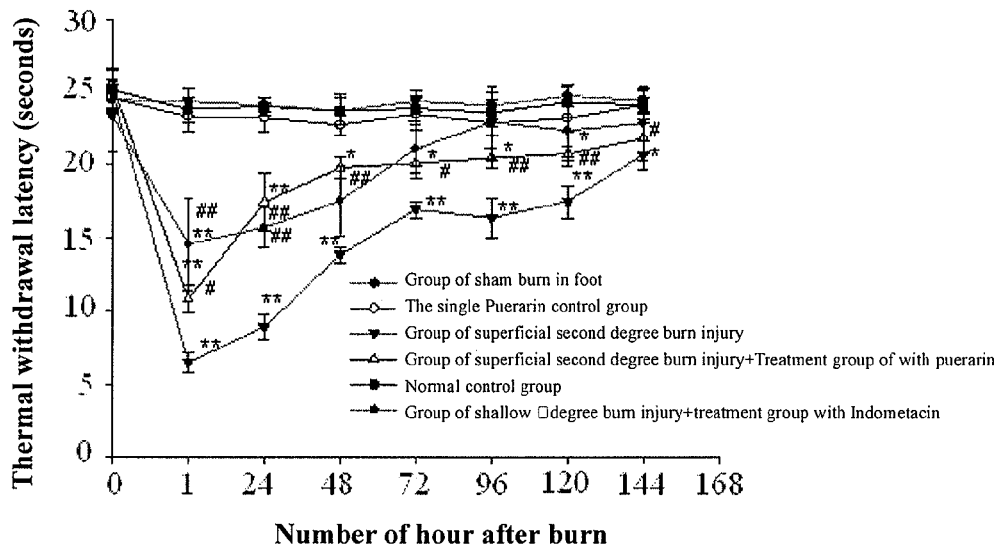
FIG. 9 is a diagram for the effects of puerarin on thermal hyperalgesia of rats that suffer from burn.

In the comparison among the group III (superficial second degree foot burn), the group IV (superficial second degree foot burn+puerarin), the group VI (superficial second degree foot burn+Indocin), the group I (sham foot burn), the group II (intraperitoneal injection of puerarin), the group V (control), the thermal withdrawal latency (TWL) in the group III and the group IV significantly decreased (p<0.01), and no significant difference was found in the comparison among the group I (sham foot burn), the group II (intraperitoneal injection of puerarin) and the group V (control) (p>0.05). The thermal withdrawal latency (TWL) in the group IV (superficial second degree foot burn+puerarin) and the group VI (superficial second degree foot burn+Indocin) significantly decreased in comparison to those of the group I (sham foot burn), the group II (intraperitoneal injection of puerarin) and the group V (control) 24 hours after burn (p<0.01), but it significantly increased in comparison to that of the group III (superficial second degree foot burn+puerarin) (p<0.01). The thermal withdrawal latency (TWL) in the group IV (superficial second degree foot burn+puerarin) and the group VI (superficial second degree foot burn+Indocin) almost recovered to normal level after 144 hours (p>0.05), while the thermal withdrawal latency in the group III (superficial second degree foot burn+puerarin) was still low (p<0.01) (see FIG. 9).

2.1.4 Detection on Mechanical Hyperalgesia in Rats that Suffer from Foot Burn:

BME-403 Von Frey fine thread was used to determine the mechanical withdrawal threshold (MWT). The rats were kept in transparent organic glass box (22×12×22 $cm^3$), and the bottom of the organic glass box was made of wire netting of 1×1 $cm^2$. The rats were raised in the laboratory after operations and they were kept in the organic glass box for accommodation for 15 minutes before the detection. The bending forces were 0.13, 0.20, 0.33, 0.60, 1.30, 3.60, 5.00, 7.30, 9.90, 20.1 g respectively, and bending forces≧20.1 g were recorded as 20.1 g. Each test was performed for ten times from the smallest bending force until the frequency of withdrawal was higher than 5/10, namely 50% reaction threshold (that was the value for inducing five reactions in ten tests. The test was repeated for three times and the average was used). The interval between two stimulation was at least more than 15 seconds until the stimulus-induced reactions (such as licking feet and throwing legs) completely disappeared.

Figure 10:
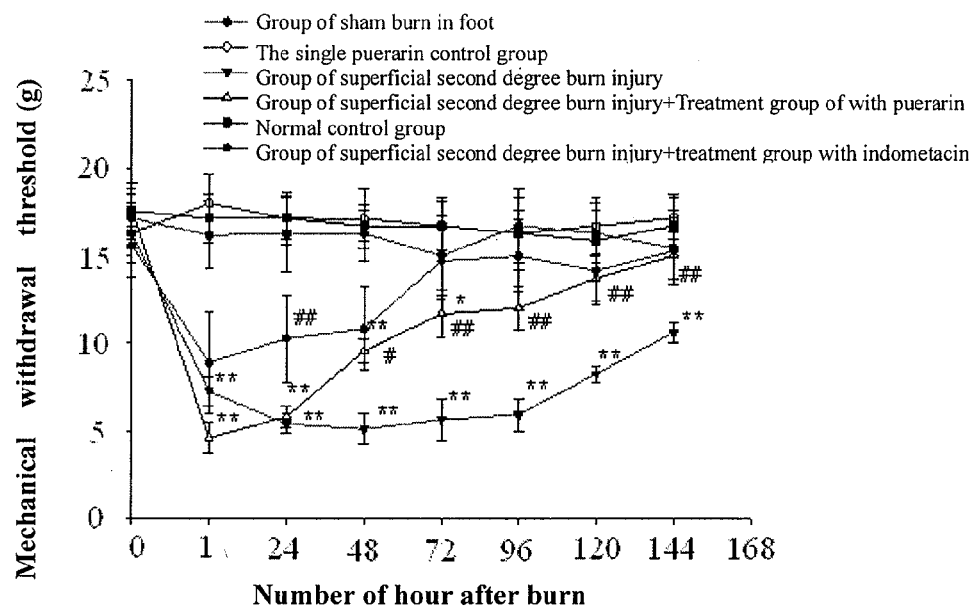
FIG. 10 is a diagram for the effects of puerarin on mechanical hyperalgesia of rats that suffer from burn.

The mechanical withdrawal threshold (MWT) in the group III (superficial second degree foot burn+puerarin), the group IV (superficial second degree foot burn+puerarin) and the group VI (superficial second degree foot burn+Indocin) significantly decreased one hour after burn in comparison to those of the group I (sham foot burn), the group II (intraperitoneal injection of puerarin) and the group V (control) (p<0.01), while no significant difference was found in the comparison among the group I (sham foot burn), the group II (intraperitoneal injection of puerarin) and the group V (control) (p>0.05). The mechanical withdrawal threshold (MWT) in the group IV (superficial second degree foot burn+puerarin) and the group VI (superficial second degree foot burn+Indocin) significantly decreased in comparison to the group III (superficial second degree foot burn+puerarin) (p<0.01). The mechanical withdrawal threshold (MWT) almost recovered to normal level after 72 hours or 96 hours in the group IV (superficial second degree foot burn+puerarin) and the group VI (superficial second degree foot burn+Indocin) in comparison to the group I, the group II and the group V (p>0.05), while the mechanical withdrawal threshold (MWT) in the group III (superficial second degree foot burn+puerarin) was still low (p<0.01). (FIG. 10).

2.1.5 Immunohistochemical Analysis on the Change in $P2X_3$ Expression in Dorsal Root Ganglion of Rats:

SD rats (their body weights were 200±20 g) were randomly divided into the group I (sham back burn), the group II (Puerarin, intraperitoneal injection), the group III (superficial second degree back burn), the group IV (superficial second degree back burn+puerarin), the group V (control) and the group VI (superficial second degree back burn+Indocin). The rats in the group IV (superficial second degree back burn+puerarin) were subjected to intraperitoneal injection of puerarin (100 mg/kg) everyday for continuous three days 30 minutes before burn and after burn. Immunohistochemical analysis was used to detect the change in $P2X_3$ expression in dorsal root ganglion in burn position of rats.

Figure 11:
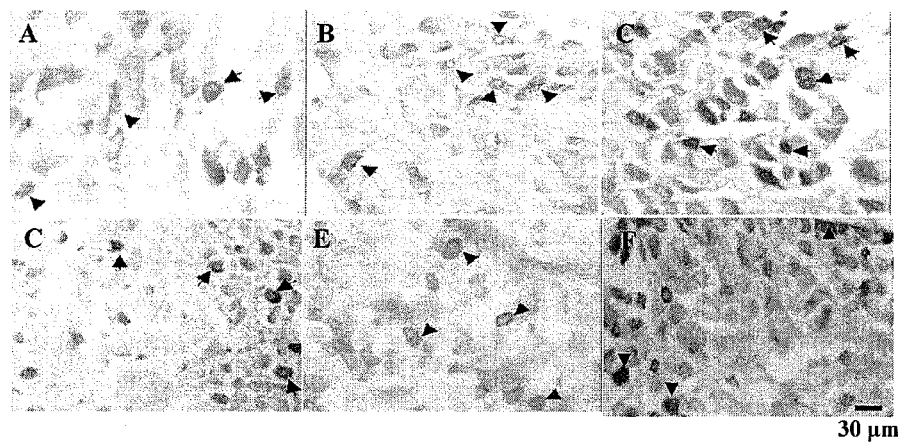
FIG. 11 are the pictures for the effects of puerarin on immunoreactivity of $P2X_3$ receptor in dorsal root ganglion of rats that suffer from burn, wherein, A: the group of sham burn; B: the single puerarin group; C: the group of superficial second degree burn; D: the group of superficial second degree burn+puerarin; E: the normal group; F: the group of chronic constriction injuries on sciatic nerve+idomethine treatment.

Results of immunohistochemical analysis were subjected to analysis by using Hmias-2000 high-resolution color medical image analysis system. The results showed that the average optical density values of the group I, the group II, the group III, the group IV, the group V and the group VI were 1.04±0.04 (n=10), 1.01±0.02 (n=10), 1.21±0.04 (n=10), 1.10±0.02 (n=10), 1.03±0.02 (n=10) and 1.16±0.03 (n=10) respectively. $P2X_3$ mRNA expression in the group III (superficial second degree two foot burn+puerarin) was significantly higher than those in the group I, the group II, the group IV and the group V ($p<0.01$), and $P2X_3$ mRNA expression decreased in the group VI (superficial second degree back burn+Indocin) in comparison to the group III (the group of superficial second degree foot burn+puerarin) ($p>0.05$), and no significant difference was found in the comparison in $P2X_3$ receptor expression among the group I, the group II and the group V ($p>0.05$); $P2X_3$ receptor expression in the group IV (superficial second degree back burn+puerarin) was slightly higher than those of the group I, the group II and the group V, but the difference was not significant ($p>0.05$), and its expression in the group IV significantly decreased in comparison to that of the group III (superficial second degree two foot burn+puerarin) ($p<0.01$), and its expression in the group IV significantly decreased in comparison to that of the group VI (superficial second degree back burn+Indocin) ($p<0.05$) (see FIG. 11).

2.1.6 In Situ Hybridization for the Detection of $P2X_3$ mRNA Expression in Dorsal Root Ganglion (DRG) of Rats:

SD rats (their body weights were 200±20 g) were randomly divided into the group I (sham back burn), the group II (Puerarin, intraperitoneal injection), the group III (superficial second degree back burn), the group IV (superficial second degree back burn+puerarin), the group V (control) and the group VI (superficial second degree back burn+Indocin). The rats in the group IV (superficial second degree back burn+puerarin) were subjected to intraperitoneal injection of Puerarin (100 mg/kg) everyday for continuous three days 30 minutes before and after burn. The rats in the group VI (superficial second degree back burn+Indocin) were subjected to intraperitoneal injection of idomethine (4 mg/kg/d) everyday for continuous three days 30 minutes before burn and after burn.

Figure 12:
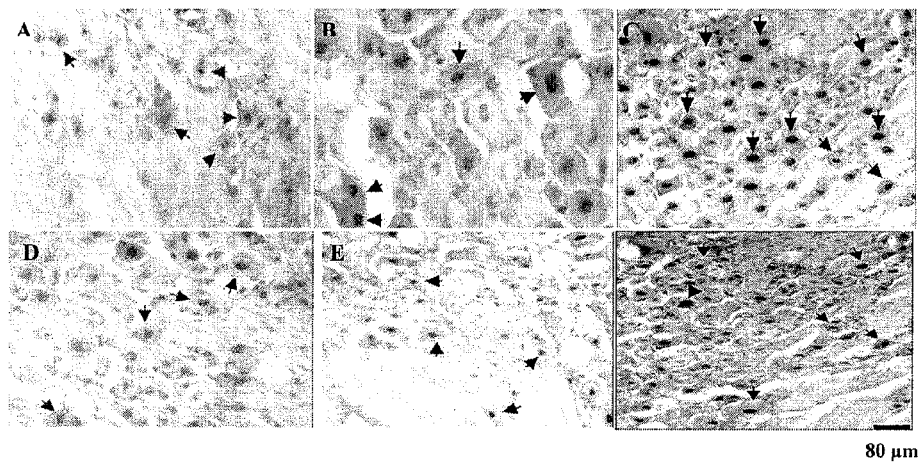
FIG. 12 are the pictures for the effects of puerarin on mRNA expression of $P2X_3$ receptor in dorsal root ganglion of rats that suffer from burn, wherein, A: the group of sham burn; B: the single puerarin group; C: the group of superficial second degree burn; D: the group of superficial second degree burn+puerarin; E: the normal group; F: the group of chronic constriction injuries on sciatic nerve+idomethine treatment.

Results of in situ hybridization were subjected to analysis by using Hmias-2000 high-resolution color medical image analysis system for the detection of $P2X_3$ receptor expression in dorsal root ganglion (DRG) in burn position of rats. The results showed that the average optical density values of the group I, the group II, the group III, the group IV, the group V and the group VI were 1.01±0.03 (n=10), 0.97±0.01 (n=10), 1.15±0.04 (n=10), 1.01±0.03 (n=10), 0.99±0.02 (n=10) and 1.06±0.05 (n=10) respectively. $P2X_3$ mRNA expression in the group III (superficial second degree back burn) was significantly higher than those of the group I, the group II, the group IV and the group V ($p<0.05$), and the difference in $P2X_3$ mRNA expression among the group I, the group II and the group V was not significant ($p>0.05$); $P2X_3$ mRNA expression in the group VI (superficial second degree back burn+Indocin) significantly decreased in comparison to that of the group III (superficial second degree back burn) ($p<0.05$); $P2X_3$ mRNA expression in DRG in the group IV (superficial second degree back burn+puerarin) significantly decreased in comparison to that of the group III (superficial second degree back burn) ($p<0.01$); $P2X_3$ mRNA expression in DRG in the group IV (superficial second degree back burn+puerarin) significantly decreased in comparison to that of the group VI (superficial second degree back burn+Indocin) ($p<0.05$); no significant difference was found in the comparison among the group I, the group II and the group V ($p>0.05$) (see FIG. 12).

2.1.7 Detection of the Change in $P2X_3$ Protein Expression in Dorsal Root Ganglion (DRG) of Rats:

SD rats (their body weights were between 200±20 g) were randomly divided into the group I (sham back burn), the group II (Puerarin, intraperitoneal injection), the group III (superficial second degree back burn), the group IV (superficial second degree back burn+puerarin), the group V (control) and the group VI (superficial second degree back burn+Indocin). The rats in the group IV (superficial second degree back burn+puerarin) were subjected to intraperitoneal injection of puerarin (100 mg/kg) everyday for continuous three days 30 minutes before burn and after burn. The rats in the group VI (superficial second degree back burn+Indocin) were subjected to intraperitoneal injection of idomethine (4 mg/kg/d) everyday for continuous three days 30 minutes before burn and after burn.

Figure 13:
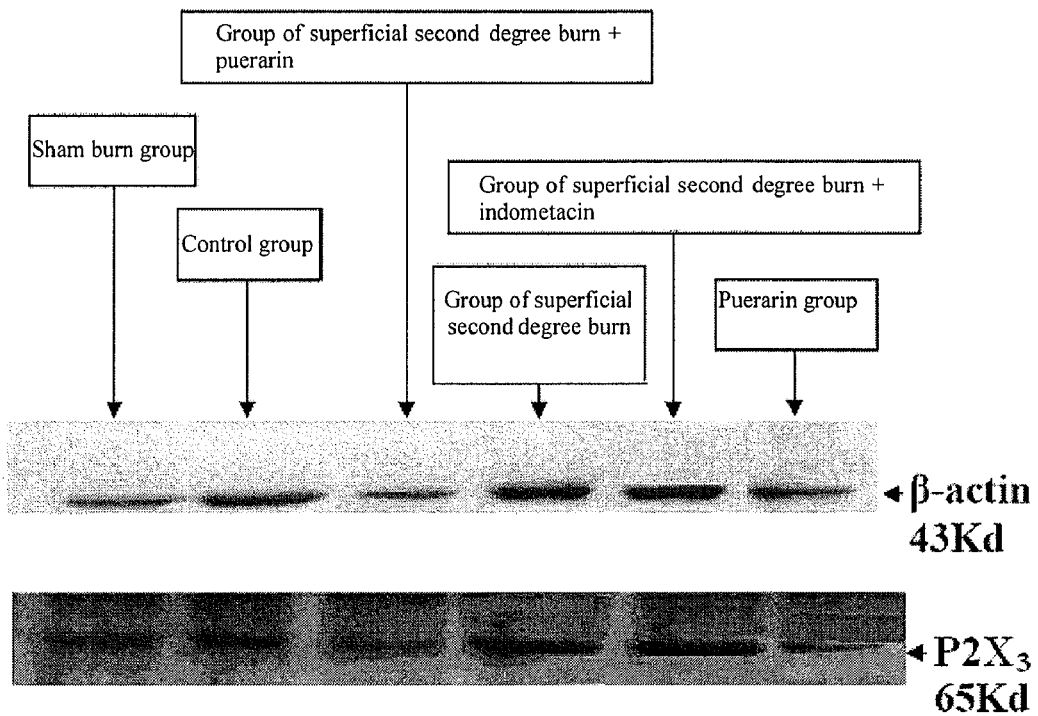
FIG. 13 is a diagram for the effects of puerarin on $P2X_3$ receptor expression in dorsal root ganglion of rats that suffer from burn, wherein the sequence of grouping in the experiment is as follows: the group of sham burn; the normal control group; the group of superficial degree second burn+puerarin; the group of superficial degree second burn; the single puerarin group; the group of chronic constriction injuries on sciatic nerve+idomethine treatment.

Results: the optical density scanned values for the interested bands that were detected on X-ray film were read by using Alpha Imager 2200 image analysis software, and the scanned values of β-actin for different groups were used to normalize the expression level of $P2X_3$ in corresponding groups. The results showed that the protein expression level of $P2X_3$ in the group I, the group II, the group IV, the group V and the group VI (after normalization with corresponding β-actin) were: 0.99±0.07 (n=3), 0.97±0.02 (n=3), 1.23±0.06 (n=3), 0.93±0.02 (n=3), 0.98±0.02 (n=3) and 1.14±0.03 (n=3) respectively. The expression of $P2X_3$ protein in the group III (superficial second degree back burn) was significantly higher than those of the group I, the group II, the group IV and the group V ($p<0.01$); the expression of $P2X_3$ protein in the group VI (superficial second degree back burn+Indocin) was lower than that of the group III (superficial second degree back burn) ($p<0.05$); no significant difference was found in the comparison in $P2X_3$ protein expression among the group I, the group II and the group V ($p>0.05$), while the relatively expression level of $P2X_3$ protein in DRG in the group IV (superficial second degree back burn+puerarin) was lower in comparison to those of the group I, the group II and the group V, but the differences were not significant ($p>0.05$), the relatively expression level of $P2X_3$ protein in DRG in the group IV (superficial second degree back burn+puerarin) significantly decreased in comparison to that of the group III (superficial second degree back burn) ($p<0.01$), and the relatively expression level of $P2X_3$ protein in DRG in the group IV (superficial second degree back burn+puerarin) significantly decreased in comparison to that of the group VI (superficial second degree back burn+Indocin) ($p<0.05$) (see FIG. 13).

2.1.8 RT-PCR Detection on the Change in $P2X_3$ mRNA Expression in Dorsal Root Ganglion (DRG) of Rats:

SD rats (their body weights were between 200±20 g) were randomly divided into the group I (sham back burn), the group II (Puerarin, intraperitoneal injection), the group III (superficial second degree back burn), the group IV (superficial second degree back burn+puerarin), the group V (control) and the group VI (superficial second degree back burn+Indocin). The rats in the group IV (superficial second degree back burn+puerarin) were subjected to intraperitoneal injection of puerarin (100 mg/kg) 30 minutes before burn and after burn everyday for continuous three days. The rats in the group VI (superficial second degree back burn+Indocin) were subjected to intraperitoneal injection of idomethine (4 mg/kg/d) 30 minutes before burn and after burn everyday for continuous three days.

Primer design: β-actin was selected as the internal reference and the sequences for the primers were as below:

```
Primer P2X₃
(the length of the product was 519 bp)
S 5'-CAACTTCAGGTTTGCCAAA-3'
A 5'-TGAACAGTGAGGGCCTAGAT-3'

Primer β-actin
(the length of the product was 240 bp)
S 5'-TAAAGACCTCTATGCCAACACAGT-3'
A 5'-CACGATGGAGGGGCCGGACTCATC-3'
```

Figure 14:
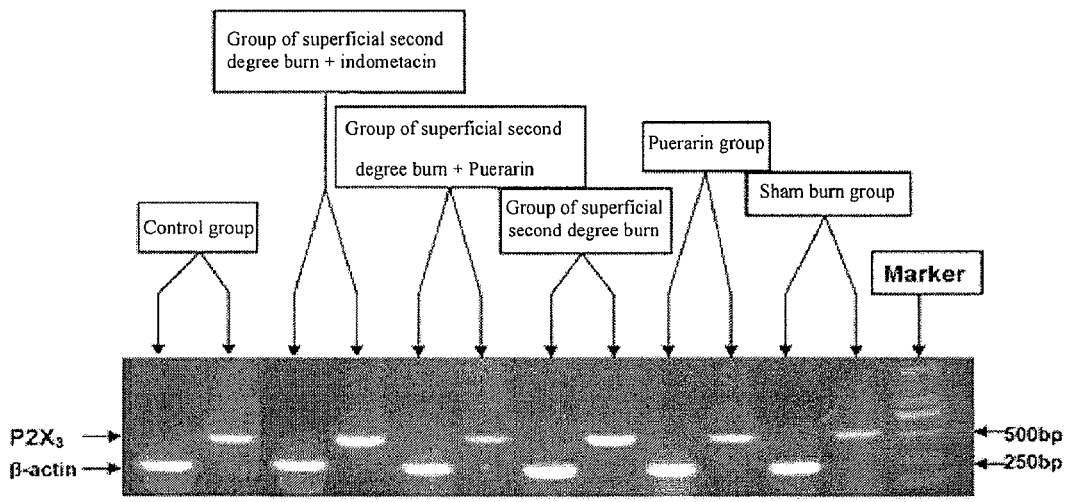
FIG. 14 is a diagram for the effects of puerarin on mRNA expression of $P2X_3$ receptor in dorsal root ganglion of rats that suffer from burn, wherein the sequence of grouping in the experiment is as follows: the normal control group; the group of superficial second degree burn+puerarin; the group of superficial second degree burn; the single puerarin group; the group of sham burn; the group of chronic constriction injuries on sciatic nerve+idomethine treatment.

Gel image system was used to record the scanned values for spot density (average optical density) of target electrophoresis bands, and the ratio between $P2X_3$ band and corresponding β-actin band was used as the relative amount of $P2X_3$ mRNA expression. The results showed that the relative expression amounts of $P2X_3$ mRNA in the group I, the group II, the group III, the group IV, the group V and the group VI (after normalization with corresponding β-actin) were 0.88±0.02 (n=3), 0.89±0.02 (n=3), 1.04±0.03 (n=3), 0.90±0.02 (n=3), 0.91±0.03 (n=3) and 0.97±0.02 (n=3). The expression of $P2X_3$ mRNA in the group III (superficial second degree back burn) was significantly higher than those of the group I, the group II, the group IV and the group V ($p<0.01$), the expression of $P2X_3$ mRNA in the group VI (superficial second degree back burn+Indocin) was lower than that of the group III (superficial second degree back burn) ($p<0.05$), and no significant difference was found in the comparison in $P2X_3$ mRNA expression among the group I, the group II and the group V ($p>0.05$), while the expression of $P2X_3$ mRNA in the group IV (superficial second degree back burn+puerarin) was significantly lower than that of the group III (superficial second degree back burn) ($p<0.01$), and the expression of $P2X_3$ mRNA in the group IV (superficial second degree back burn+puerarin) was significantly lower than that of the group VI (superficial second degree back burn+Indocin) ($p<0.05$), and no significant difference was found in the comparison among the group I, the group II and the group V ($p>0.05$) (see FIG. 14).

The applicant have found that puerarin can alleviate the pain behavioral responses of rats that suffer from neuropathic pain and burn pain by the research in the laboratory. The treatment group with non-steroid anti-inflammatory analgesic can significantly alleviate the mechanical and thermal hyperalgesia reactions of CCI models of rats and those suffer from burn pain, but the effects on $P2X_3$ receptor expression in primary sensory nerve cells of DRG in CCI models of rats and those suffer from burn pain are lower than that of the puerarin treatment group. Since it has been shown that puerarin can decrease $P2X_3$ receptor expression in neurons from dorsal root ganglion of rats that suffer from neuropathic pain and burn pain, and it can also inhibit the $P2X_3$ receptor agonist ATP- and α,β-meATP-activated electric current in neurons from dorsal root ganglion of normal rats that suffer from nervous pathological pain and burn pain, it indicates that the mechanism for puerarin to alleviate pain is to block the transmission of $P2X_3$ receptor mediated pain information and it can prevent and cure pain. Furthermore, since P2X purinoceptor is involved in many physiological functions and pathological effects in the body, the exploration of new specific blocking agent for purinoceptor will significantly promote the research work on in vivo physiological functions and pathological effects of purine information system.

Embodiment 1

The oral, injectable or locally applied (such as local dressing) puerarin preparations for the treatments on acute pain/chronic pain are produced by using well known method in the art. The experimental results in comparison to those from the treatment group with non-steroid anti-inflammatory analgesic for rats indicated that puerarin took effects on $P2X_3$ receptor and produced pain relieving effects. The adverse effects in comparison to opioid and other analgesics were significant, and it is liable to lead to drug tolerance, drug dependence and withdrawal syndrome, and the toxic and adverse effects of idomethine and other anti-inflammatory and analgesic drugs are significant, toxic and adverse effects of active ingredients in Chinese medicines are not obvious, puerarin is a kind of drug that has been applied in clinical study on cardiovascular diseases, which is helpful for its development and applications as a kind of analgesic drug.

Embodiment 2

The oral, injectable or locally applied (such as local dressing) puerarin preparations for the treatments on $P2X_3$ receptor mediated nervous system diseases are produced by using well known method in the art. The experimental results in comparison to those from the treatment group with non-steroid anti-inflammatory analgesic for CCI model of rats and those suffered from burn pain indicated that it can significantly alleviate mechanical and thermal hyperalgesia of rats, but the effects on $P2X_3$ receptor expression in primary sensory nerve cells of DRG in CCI model of rats and those suffered from burn pain were lower than that of the puerarin treatment group, indicating that the mechanism for analgesic effects of puerarin is different from that of idomethine, and puerarin can take effects by reducing the expression of $P2X_3$ receptor, which further indicates that puerarin may be used as a drug for prevention and treatment on $P2X_3$ receptor mediated nervous system diseases.

What is claimed is:

1. A method of treating neuropathic pain mediated by P2X$_3$ receptor in a mammal in need thereof comprising administering puerarin to the mammal in need of treatment in an amount effective to treat the neuropathic pain.

2. A method of treating acute pain caused by burn injury mediated by P2X$_3$ receptor in a mammal in need of treatment comprising administering puerarin to the mammal in need of treatment in an amount effective to treat acute pain caused by burn injury.

\* \* \* \* \*

UNITED STATES PATENT AND TRADEMARK OFFICE
CERTIFICATE OF CORRECTION

PATENT NO. : 8,362,070 B2  Page 1 of 1
APPLICATION NO. : 12/922245
DATED : January 29, 2013
INVENTOR(S) : Liang et al.

It is certified that error appears in the above-identified patent and that said Letters Patent is hereby corrected as shown below:

In the Drawings:

Sheet 1 of 7 (Y-Axis, FIG. 1) at line 1, Change "atency" to --latency--.

Sheet 6 of 7 (FIG. 11) at line 2 (approx.), Change "C" to --D--.

In the Specifications:

In column 2 at line 47, Change "lysomal" to --lysosomal--.

In column 2 at line 56, Change "on" to --of--.

In column 4 at line 59, Change "Indo)." to --Indocin).--.

In column 5 at line 15 (approx.), Change "triphophate" to --triphosphate--.

In column 5 at line 20, Change "tnternal" to --internal--.

In column 6 at line 2, Change "100" to --00--.

In column 6 at line 56, Change "peroxydase" to --peroxidase--.

In column 7 at line 1, Change "peroxydase" to --peroxidase--.

In column 7 at line 17-18, Change "(Dubecco's" to --(Dulbecco's--.

In column 8 at line 56, Change "50 mg/mL." to --50 mg/mL,--.

In column 9 at line 10, Change "Chinese." to --Chinese--.

In column 12 at line 34, Change "vim." to --µm.--.

In column 13 at line 58, Change "irrdiate" to --irradiate--.

Signed and Sealed this
Third Day of September, 2013

Teresa Stanek Rea
*Acting Director of the United States Patent and Trademark Office*

SEQUENCE LISTING

<160> NUMBER OF SEQ ID NOS: 2

<210> SEQ ID NO 1
<211> LENGTH: 3713
<212> TYPE: DNA
<213> ORGANISM: Rattus norvegicus
<220> FEATURE:
<221> NAME/KEY: CDS
<222> LOCATION: (182)...(1375)

<400> SEQUENCE: 1

```
atcaagggga gagactaggc actgggctac agttgcctgg cttacaggaa ctggctcttt      60
tcctcaagcc tcattaagca gcccactcca gttcttgatc tttgtctccc agtcctgaag     120
tcctttctct ccttaggctg catccacagc ccttctaagt ggctgtgagc agtttctcaa     180
tatgaactgt atatcagact tcttcaccta cgagactacc aagtcggtgg ttgtgaagag     240
ctggaccatt gggatcatca accgagccgt ccagctgctg attatctcct actttgtggg     300
gtgggttttc ttgcatgaga aggcctacca agtgagggac accgccattg agtcctcagt     360
agttacaaag gtgaaaggct cgggcgcta tgccaacaga gtcatggacg tgtcggatta     420
tgtgacccca ccccagggca cctctgtctt tgtcatcatc accaaaatca tcgttactga     480
aaatcaaatg caaggattct gtccagagaa tgaagagaag taccgctgtg tgtctgacag     540
ccagtgtggg cctgaacgct tcccaggtgg ggggatcctc accggccgct gcgtgaacta     600
cagctctgtt ctccggacct gtgagatcca gggctggtgc cccactgagg tggacaccgt     660
ggagatgcct atcatgatgg aggctgagaa cttcaccatt ttcatcaaga acagcatccg     720
tttccctctc ttcaactttg agaagggaaa cctcctgcct aacctcaccg acaaggacat     780
aaagaggtgc cgcttccacc ctgaaaaggc cccattttgc cccatcttga gggtagggga     840
tgtggttaag tttgctggac aggattttgc caagctggcc cgcacgggtg gcgttctggg     900
tattaagatc ggctgggtgt gcgatctaga caaggcctgg gaccagtgca tccctaaata     960
ttccttcact cggctggatg gagtttctga gaaaagcagt gtttccctg gctacaactt    1020 caggtttgcc aaatactata agatggagaa cggcagcgag taccgcacac tcctgaaggc    1080
ttttggcatc cgctttgatg tgctggtata tgggaacgct ggcaagttca acatcatccc    1140
caccattatc agctcggtgg cggccttcac ttctgtggga gtgggcactg ttctctgtga    1200
catcatcctg ctcaatttcc tcaaggggc tgatcactac aaagccagga gtttgagga    1260 ggtgactgag acaacactga agggtactgc gtcaaccaac ccagtgttcg ccagtgacca    1320
ggccactgtg gagaagcagt ctacagactc aggggcctat tctattggtc actagggcct    1380
cttcccaggg ttccatgctc acccttaggc tgcagaacct gcaaacaggc cactctatct    1440
aagcagtcag gggtgggagg gggagaagaa gggctgctat ttctgctgtt cacccccaaag    1500 actagatcca gatatctagg ccctcactgt tcaacagata ggcaatgctt cccactaaga    1560
cttgaatctt gccttacc cttgcatgcc tcccacctgc ttccctggat cccaggacag    1620
cagcatccac ccctttccaa aggattgaga aaatggtagc taaggttaca cccataggac    1680
ctaccacgta ccaagcactt ccacacatat tatccctttt cacccttaaa ataatcctat    1740
aaggtagatt tcttggggttg tttgtttgtt ttgttattaa gagaagcaaa ggcccaggga    1800
gaccgaggcg tttgccccag gccatgtagc taggaagtga gatctacacc ctggctagcc    1860
cttctgccca catctgtaat ggaagaatga actctctagg catctaccct tctgtgtcag    1920 ttgccttttcc ctgccttccc atgatgccca acagtgagct ttttcaggaa tgcagcccta    1980
ctttagggga gcccacggaa atgcagaagg aaatagctgt gactatcagt gattttttcct    2040 tgcctcaccc catatgcgaa gctcaagctg agggagagac ctttattctc caatgaggtc    2100
ctcacacatc cacacatctg ggccctcact ccggaatcta gacagaaaac acacacatac    2160
atgaccgaca agaggcaatt tctaaccta gcaccatgtc ccagtacatc agctgtctta    2220
gtttatagca ctgttgggaa agccatggtt aggggctggg gatgtagttg ggtaggtaga    2280
gtgtttgtct agtatgttag ccctaagacc aacctgcagc acttcataaa ccaggcacac    2340
```

-continued

| | |
|---|---|
| ttgtaatccc agcactcggg aggtaggcat ggaggatcaa aagttcgagt ttatccttgc | 2400 |
| caacgcaata agtgtgaacc ttgcctggaa cccatgaaac tgtttcaaaa tagaagtggg | 2460 |
| gagacccagt aagacccaat accttgtgag cattcagcca gggcagcaag gcctgttttc | 2520 |
| acaggatcct aacaggtgat caggtaggag ctaaaggagc tcagagacc atcatgtcta | 2580 |
| ggcctcttgc ttactgatca ttaaccctga ggccaaaacc gaaaaatttc ttgccttgtg | 2640 |
| ccattgtgag gccccaagag agacacaggt gtcctgtgca ttataagctg aagacaagtt | 2700 |
| cacattgtct ccatagccca gatgtcccat ctcctttctg agcttttaaa gaaaacaaga | 2760 |
| gatgttgagg aagctctaaa tgtagcgcac aaaactcaag acagatcaa ggtgtaggaa | 2820 |
| agaagcaggt tgagaggctc ttttggtttg gtttgtttat ttggttggtt ggttggttgg | 2880 |
| ttacagatct ctctcaactc aacttttccc cagtatttgg atctgcaggc aagcgccatt | 2940 |
| atacggcagg gggcatctct tttaaaagaa tatatgatta agtatcagaa aagttcatgc | 3000 |
| aaatcagtgg gcctgaggta tacatttaat taatatcagg gccaatctgc ctcttaaaca | 3060 |
| tgggcttgat gctgagagct tagaagagat gagcattcat gtggacagag ggctggccct | 3120 |
| caccggacga gatgagcatt catgtggaca gagggctggc cctcaccgga cggtgcaaag | 3180 |
| agatgtggga gagggagagt ctaggaggac cacaggagtt ctcacacaga cccaacctca | 3240 |
| atgatgccca ccccagggggg agaaggggggt aagagtcctt cccactagcc ttgcatcaat | 3300 |
| ccttttcttc cctctccttt ccccacagcc cccatcataa tgtgtgatgg ggtactgtct | 3360 |
| ccctaacacc agtgtcaatt cctgggtagt atccagagac ctggccaggc ttcatctctc | 3420 |
| caatagagac atcaggaaag gaaagagcac agcctccaag aaggtagctt atagcccctc | 3480 |
| attgggcaag gctgagttca ccaagatgct ccctagaaga agatggagac acgtgtccta | 3540 |
| agaggatctc atacccccaga ctagaataat tcttccccac atgcctggac ctcttctggg | 3600 |
| ccttcagtaa gtgtgtaaac tccatgctgt actctccttg tctgaaccaa gtccacttcg | 3660 |
| atgtgctaga tgtcagctaa tcatagaaat tacaacgacc agcttgtatc tga | 3713 |

<210> SEQ ID NO 2
<211> LENGTH: 1296
<212> TYPE: DNA
<213> ORGANISM: Rattus Norvegicus
<220> FEATURE:
<221> NAME/KEY: CDS
<222> LOCATION: (82)...(1209)

<400> SEQUENCE: 2

| | |
|---|---|
| ggggtcgagt ccgcgtccac ccgcgagtac aaccttcttg cagctcctcc gtcgccggtc | 60 |
| cacacccgcc accagttcgc catggatgac gatatcgctg cgctcgtcgt cgacaacggc | 120 |
| tccggcatgt gcaaggccgg cttcgcgggc gacgatgctc ccgggccgt cttcccctcc | 180 |
| atcgtgggcc gccctaggca ccagggtgtg atggtgggta tgggtcagaa ggactcctac | 240 |
| gtgggcgacg aggcccagag caagagaggc atcctgaccc tgaagtaccc cattgaacac | 300 |
| ggcattgtca ccaactggga cgatatggag aagatttggc accacacttt ctacaatgag | 360 |
| ctgcgtgtgg cccctgagga gcaccctgtg ctgctcaccg aggcccctct gaaccctaag | 420 |
| gccaaccgtg aaaagatgac ccagatcatg tttgagacct tcaacacccc agccatgtac | 480 |
| gtagccatcc aggctgtgtt gtccctgtat gcctctggtc gtaccactgg cattgtgatg | 540 |
| gactccggag acggggtcac ccacactgtg cccatctatg agggttacgc gctccctcat | 600 |
| gccatcctgc gtctggacct ggctggccgg gacctgacag actacctcat gaagatcctg | 660 |
| accgagcgtg gctacagctt caccaccaca gctgagaggg aaatcgtgcg tgacattaaa | 720 |

```
gagaagctgt gctatgttgc cctagacttc gagcaagaga tggccactgc cgcatcctct    780
tcctccctgg agaagagcta tgagctgcct gacggtcagg tcatcactat cggcaatgag    840
cggttccgat gccccgaggc tctcttccag ccttccttcc tgggtatgga atcctgtggc    900
atccatgaaa ctacattcaa ttccatcatg aagtgtgacg ttgacatccg taaagacctc    960
tatgccaaca cagtgctgtc tggtggcacc accatgtacc caggcattgc tgacaggatg   1020
cagaaggaga ttactgccct ggctcctagc accatgaaga tcaagatcat tgctcctcct   1080
gagcgcaagt actctgtgtg gattggtggc tctatcctgg cctcactgtc caccttccag   1140
cagatgtgga tcagcaagca ggagtacgat gagtccggcc cctccatcgt gcaccgcaaa   1200
tgcttctagg cggactgtta ctgagctgcg ttttacaccc tttctttgac aaaacctaac   1260
ttgcgcaaaa aaaaaaaaaa aaaaaaaaaa aaaaaa                              1296
```